United States Patent [19]
Heckenmüller et al.

[11] Patent Number: 5,514,673
[45] Date of Patent: May 7, 1996

[54] PHARMACEUTICAL COMPOSITION CONTAINING LIPOPHILIC DRUGS

[75] Inventors: Harald Heckenmüller, Hamburg; Gerd Kutz, Detmold, both of Germany

[73] Assignee: Astra Aktiebolag, Sodertalje, Sweden

[21] Appl. No.: 224,164

[22] Filed: Apr. 7, 1994

[30] Foreign Application Priority Data

Apr. 7, 1993 [SE] Sweden ................... 9301171

[51] Int. Cl.$^6$ ................... A61K 9/113; A61K 31/56
[52] U.S. Cl. ................... 514/177; 514/182; 514/899; 514/938; 552/607; 552/625; 424/434; 424/450
[58] Field of Search ................... 424/450, 434; 514/938, 899, 177, 182; 552/607, 625

[56] References Cited

U.S. PATENT DOCUMENTS

| | | | |
|---|---|---|---|
| 4,053,489 | 10/1977 | Wirth | 514/899 |
| 4,078,060 | 3/1978 | Benson | 514/182 |
| 4,096,254 | 6/1978 | Benson | 514/899 |
| 4,383,993 | 5/1983 | Hussain et al. | 514/182 |
| 4,396,615 | 8/1983 | Petrow et al. | 514/899 |
| 4,596,795 | 6/1986 | Pitha | 514/58 |
| 4,742,046 | 5/1988 | Bliah | 514/888 |
| 4,963,367 | 10/1990 | Ecanow | 424/455 |
| 5,115,805 | 5/1992 | Bommannan et al. | 604/20 |
| 5,120,546 | 6/1992 | Hansen et al. | 424/449 |
| 5,152,923 | 10/1992 | Weder et al. | 514/938 |
| 5,364,632 | 11/1994 | Benita et al. | 424/450 |

FOREIGN PATENT DOCUMENTS

| | | |
|---|---|---|
| 0371496 | 6/1990 | European Pat. Off. . |
| 0391369 | 10/1990 | European Pat. Off. . |

OTHER PUBLICATIONS

Duchateau, G., Dissertation, University of Leiden 1980.
Hussein, A., et al. "Nasal Absorption of Propanol from different dosage forms . . . " J. Pharmaceutical Sciences 69 (1980) 1411.
Kublik, H. "Optimierung von Arzneistoffzubereitungen Zur Nasalen Applikation 1993" Dissertation, Kiel.

*Primary Examiner*—Ronald W. Griffin
*Attorney, Agent, or Firm*—White & Case

[57] ABSTRACT

A pharmaceutical composition having a form suitable for transmucosal administration containing progesterone and/or 17-β-estradiol as an active ingredient.

14 Claims, No Drawings

PHARMACEUTICAL COMPOSITION CONTAINING LIPOPHILIC DRUGS

BACKGROUND OF THE INVENTION

The present invention relates to a pharmaceutical composition having a formulation and form suitable for transmucosal administration and containing a lipophilic drug such as sex hormones or combinations of sex hormones. The natural forms of these hormones are particularly suitable for the mentioned pharmaceutical composition.

BACKGROUND ART

Progesterone and 17β-estradiol are the most active natural human sex hormones. Because of their very limited oral effectiveness, resulting from a high first pass effect, these natural sex hormones have been replaced by synthetic and semisynthetic derivatives for virtually all medical applications. It is, however, known from literature that these synthetic derivatives have negative side effects, especially on protein synthesis. This is, also according to literature in the field, in contrast to the natural sex hormones.

For the above reason, there is a clear and long felt need for better non-oral compositions and dosage forms of the natural sex hormones. In order to offer high flexibility in their therapeutical use such dosage forms should ensure low physiological levels of the natural sex hormones while at the same time leaving the option to adapt the dose of the hormone to the individual therapeutic needs.

Parenteral administration circumvents the undesired first pass effect. There are, however, obvious inconveniences associated with parenteral, for example intravenous or intramuscular drug administration such as the need for sterile delivery devices, pain and irritation caused by reiterated injections and the potential risk of infections. Another disadvantage is that the patient normally needs medical assistance in administering. Therefore, alternative means of drug delivery, equally effective in the sense that first-pass metabolism is circumvented have been sought.

Transdermal drug delivery as another parenteral route implicates the risk of skin irritations. It also leaves very limited possibilities to adjust the dose and frequency of application to all therapeutic goals and individual needs.

One promising alternative to the above mentioned routes is drug administration via the transmucosal route. However, just as in the case with other methods for non-invasive medication the bioavailability of a drug after transmucosal administration is largely unpredictable, depending inter alia on the chemical nature of the drug and the drug delivery system. The following attempts have been made to design transmucosal, preferably nasal drug delivery systems of natural sex hormones.

In *J. Clin. Endocrinol. Metab.* 45, 1977 pp. 1261–1264, Rigget al. it has been demonstrated that intranasal administration of estradiol in a physiological saline solution is unsuitable.

In U.S. Pat. No. 4,383,993, Hussain et al. suggested an aqueous solution of the sex hormones in isotonic saline containing a surfactant such as Tween 80 as a, solubilizer. Because of its apolar character this adjuvant must be conceived as accomplishing the dissolution of the active substance in a monodispersed hydrophilic system. Systems containing such solubilizers often do not fulfill the required therapeutical needs. The reason for this is that, due to the limited solubilisation capacity, the required solubilizer concentration causes irritation of the mucosa or, as in the case of nasal administration, the volume to be applied is too high.

In European Patent No. EP 0349091 it is stated that the use of dimethyl-β-cyclodextrin as an absorption enhancer together with estradiol or progesterone ensures a suitable drug delivery system for nasal administration of natural sex hormones. This system is known to have major disadvantages connected with dimethyl-β-cyclodextrin because of its nephrotoxicity and haemolytic activity. It can also be expected that the extremely high complex binding constant of the cyclodextrin-sex hormone complex may adversely influence the drug uptake. This has, indeed, been proven to be the case in animal tests. For sublingual and buccal administration, however, the use of dimethyl-β-cyclodextrin in sex hormone compositions has virtually no effect on the absorption according to Pitha, U.S. Pat. No. 4,596,795. This, according to the same inventor, is in contrast to the uptake from aqueous solutions prepared by dissolving the hormones by means of poly-β-cyclodextrin and hydroxypropyl-β-cyclodextrin. This inventor stresses that a dissolved form of the natural sex hormones does not per se guarantee effective drug uptake through mucous membranes.

The use of an emulsion for nasal application is known from European Patent No. 0272097. This patent refers to nasal administration of pharmacologically active polypeptides together with a phospholipid such as a phosphatidylcholine, which is a lecithin, preferably admixed with a vegetable oil. The resulting system is characterized in that the water soluble active drug is located in the coherent, hydrophilic outer phase of a two phase system consisting of oil in water. A lecithin which is described in detail in this patent has proven to be an adjuvant which is effective in promoting the polypeptide uptake. The addition of a vegetable oil is useful for stabilizing the emulsion.

DISCLOSURE OF THE INVENTION

It is an object of the present invention to provide compositions which are suitable for the transmucosal administration of 17-β-estradiol or progesterone, in particular the natural types of these hormones, or mixtures thereof via the nasal route and which ensure an especially effective transmucosal absorption of the hormones avoiding the above mentioned disadvantages.

According to the invention the active drug is dissolved in an artificial or natural oil, constituting the incoherent inner phase of a two-phase system characterized in that the incoherent, lipophilic phase upon administration to mucous surfaces has no direct contact to the hydrophilic mucosa and, furthermore, enhances the lipophilic character of the incorporated drugs. Surprisingly, this emulsion ensures an effective and rapid uptake of the natural sex hormones dissolved in the lipophilic droplets.

Artificial or natural oils or mixtures thereof can be used. Examples of-natural oils are middle chained triglycerides.

The effective uptake of the sex hormones is in contrast to all described formulations for transmucosal drug delivery. Such formulations normally as a common characteristic improve the hydrophilicity in the case of hydrophobic drugs and/or ensure an immediate and direct contact to the mucosa in the case of hydrophilic drugs to be administered.

In addition to the above mentioned advantages the absorption of the sex hormone from the formulations of the present invention the absorption is not influenced by the emulsifying agent and is not restricted to separate formulations of estradiol or progesterone. Consequently, the natural sex hormones can be administered as fixed combinations.

METHOD OF PREPARATION

The formulations of the invention can be manufactured by conventional methods for preparing two-phase emulsion systems.

The sex hormones progesterone and/or 17-β-estradiol are dissolved in the oil to be used. The oil phase is admixed with the water phase and other components for further processing. In order to ensure a highly dispersed and stable system the droplets of the lipophilic incoherent inner phase are reduced to a maximal size smaller than 10μ or, preferably, smaller than 5μ. A high shear mixer and, subsequently, a high pressure homogenizer can be used for this purpose.

PHARMACEUTICAL FORMULATIONS

In principle the formulations contain the following components:

1. The sex hormones in a concentration to ensure a single dose of 3 μg– 0.5 mg of 17-β-estradiol and/or 0.1–10 mg of progesterone.
2. An artificial or natural oil or mixtures thereof in a concentration of between 5 and 50% by weight related to the whole composition. The oil or oil mixtures are characterized in that the solubility for estradiol must be at least 0.5% by weight and for progesterone at least 2%.
3. A lecithin from egg or soy bean or mixtures thereof in a concentration from 0.5 to 10% by weight.

The lecithin can be predissolved in an oily liquid of the type "ready to use" of which the main component is middle chained triglycerides for example caprylic/capric triglycerides and mixtures thereof.

4. Optionally, an additional, nonionic emulsifier such as Tween 80, Pluronic F68, Brij 96, Cremophor EL or Solution Hs 15 is added to improve the physical stability of the emulsion system. The concentration of this nonionic surfactant is limited to a concentration suitable for nasal administration, preferably about 2% by weight.
5. Optionally, also minor components having the object of adapting the formulation to the physiological needs of the nasal mucosa can be added. Such additives are preservatives such as benzalkonium chloride or chlorhexidine acetate/gluconate, agents such as glycerol, sorbitol, mannitol, xylitol or sodium chloride for forming an isotonic solution, complexing agents such as sodium edetate and/or swelling agents such as methyl hydroxypropyl cellulose or carbomer.

EXAMPLE 1

Nasal formulation. Weights in g. One unit dose is 0.5 ml containing 6.00

| | |
|---|---|
| Progesterone | 1.2 |
| Miglyol ® 812N | 47.3 |
| Lecithin (soy bean) | 1.95 |
| NaOH (0.01 M) | 18.0 |
| Na-EDTA | 0.1 |
| Glycerol | 1.1 |
| Water | ad 100 ml |

EXAMPLE 2

Nasal formulation. Weights in g. One unit dose is 0.5 ml containing 0.34 mg estradiol.

| | |
|---|---|
| Estradiol | 0.068 |
| Miglyol ® 812N | 47.3 |
| Lecithin (soy bean) | 1.95 |
| NaOH (0.01 M) | 18.0 |
| Na-EDTA | 0.1 |
| Glycerol | 1.1 |
| Water | ad 100 ml |

EXAMPLE 3

Nasal formulation. Weights in g. One unit dose is 0.5 ml containing 0.34 mg estradiol and 6.00 mg progesterone.

| | |
|---|---|
| Estradiol | 0.068 |
| Progesterone | 1.2 |
| Miglyol ® 812N | 47.3 |
| Lecithin (soy bean) | 1.98 |
| NaOH (0.01 M) | 18.0 |
| Na-EDTA | 0.1 |
| Glycerol | 1.1 |
| Water | ad 100 ml |

EXAMPLE 4

Nasal formulation. Weights in g. One unit dose is 0.34 ml containing 0.2312 mg estradiol and 4.08 mg progesterone.

| | |
|---|---|
| Estradiol | 0.068 |
| Progesterone | 1.2 |
| Miglyol ® 812N | 47.3 |
| Lecithin (soy bean) | 1.95 |
| NaOH (0.01 M) | 18.0 |
| Na-EDTA | 0.1 |
| Glycerol | 1.1 |
| Water | ad 100 ml |

EXAMPLE 5

Nasal formulation. Weights in g. One unit dose is 0.62 ml containing 0.34 mg estradiol and 6.00 mg progesterone.

| | |
|---|---|
| Estradiol | 0.055 |
| Progesterone | 0.967 |
| Miglyol ® 812N | 34.1 |
| Lecithin (egg) | 1.36 |
| Glycerol | 1.6 |
| Water | ad 100 ml |

EXAMPLE 6

Nasal formulation, Weights in g, One unit dose is 0.5 ml containing 0.34 mg estradiol and 6.00 mg progesterone.

| | |
|---|---|
| Estradiol | 0.068 |
| Progesterone | 1.2 |
| Miglyol ® 812N | 47.3 |
| Lecithin (soy bean) | 1.95 |
| NaOH 0.01 M | 18.0 |
| Na-EDTA | 1.1 |
| Glycerol | 1.1 |
| Tween ®80 | 1.1 |
| Water | ad 100 ml |

EXPERIMENTAL RESULTS

The superiority of the formulations of the present invention to known formulations was proven in a series of in vivo experiments, The single formulations were filled into two heat sterilized glass bottles, Polymer pump systems equipped with adapters were employed for the spraying operation.

After filling of the dosage spraying bottles the amount of the drug per puff was determined using a HPLC analytical method, The dosing accuracy was determined experimentally from repeating the puff 10 times and analysing the amount of drug in each ejection.

The animal model for nasal uptake of estradiol/progesteron can be described as follows:

The animals used for the experiments were adult sheep of mixed race. The animals were kept under constant veterinary control.

Before the application of the drug to each animal five puffs were made from the dosing flask. Immediately thereafter one puff was sprayed into each nostril of the animal.

Blood samples were taken alternately from both jugular veins. A reference sample was taken from each animal before the application of the drug. Samples were taken at 5, 10, 20, 30, 40, 60, 90, 120, 180 and 300 minutes after application. The samples were allowed to coagulate at room temperature for 40 minutes whereafter they were centrifugated and kept in a refrigerator until the serum was collected. The serum was kept at −70° C.

Each formulation was applied to four animals.

Analytical method: For the determination of the hormone concentration in serum samples an enzymatic immunoassay was employed. The measuring range for estradiol was 0–1500 pmol/l respectively 0–4086 pg/ml and for progesteron 0–160 nmol/l respectively 0–50.3 ng/ml.

Statistical treatment of data: The area under the curve (AUC) was calculated according to the trapezoid rule with reference to the last data point (Time 0–300 min). In the calculation of the mean residence time (MRT) the time mean values were employed (0–244 min). The calculations were performed in order for the mean value and the standard deviation to be calculated each time.

In the first series of animal model experiments it was found that the absorption kinetic characteristics for both sex hormones formulated according to the present invention in which the natural sex hormones are dissolved in the incoherent phase of a dispersed system "oil in water" is nearly identical to formulations based on purely hydrophilic systems. Furthermore, the concentration/time blood profile after nasal administration of the hormones formulated according to the present invention is similar to the same profile after intravenous administration of the natural sex hormones in dissolved form.

Intramuscular administration of oily solutions of sex hormones, according to literature, is used to obtain prolonged drug release. It should, therefore, be expected that the use of an emulsion system of the type "oil in water" with incorporated lipophilic drugs, here sex hormones, should result in a flat but prolonged absorption kinetic curve if the drugs are taken up at all. The above experimental result, which is contrary to this, was unexpected considering that the residence time in the nasal cavity for liquid formulations according to literature in the field is limited to a few minutes due to ciliary movement of the mucous tissue.

We claim:

1. A pharmaceutical composition for transmucosal administration based on progesterone and/or 17-β-estradiol as an active ingredient characterized in that the active ingredient is dissolved in an oil constituting the incoherent inner phase of an oil-water two-phase system.

2. A pharmaceutical composition according to claim 1 characterized in that at least one of progesterone or 17-β-estradiol is a natural sex hormone.

3. A pharmaceutical composition according to claim 1 characterized in that the oil is a natural oil.

4. A pharmaceutical composition according to claim 1 characterized in that the oil is an artificial oil.

5. A pharmaceutical composition according to claim 1 characterized in that the oil is a mixture of a natural oil and an artificial oil.

6. A pharmaceutical composition according to claim 1 characterized in that the solubility of progesterone in the oil phase is at least 2% by weight.

7. A pharmaceutical composition according to claim 1 characterized in that the solubility of 17-β-estradiol in the oil phase is at least 0.5% by weight.

8. A pharmaceutical composition according to claim 1 characterized in that it contains 3 μg to 0.5 mg of estradiol and/or 0.1–10 mg of progesterone.

9. A pharmaceutical composition according to claim 1 for nasal administration.

10. A pharmaceutical composition according to claim 1 containing pharmaceutically acceptable excipients together with the active compound(s).

11. A pharmaceutical composition according to claim 1 in unit dosage form.

12. A process for the manufacture of a pharmaceutical preparation according to claim 1 characterized in that progesterone and/or 17-β-estradiol is dissolved in an oil phase whereby the inner phase of an oil in water two phase system for transmucosal administration is obtained.

13. A process for the manufacture of a pharmaceutical preparation according to claim 1 wherein the oil phase is admixed with the water phase.

14. A method of administering progesterone and/or 17-β-estradiol to a mammal by transmucosal delivery comprising applying an effective amount of the composition of claim 1 to the mucosal membrane of the mammal.

* * * * *